United States Patent
Anderskewitz et al.

(10) Patent No.: US 7,544,806 B2
(45) Date of Patent: Jun. 9, 2009

(54) PIPERIDINE-SUBSTITUTED INDOLES-OR HETERODERIVATIVES THEREOF

(75) Inventors: Ralf Anderskewitz, Laupheim (DE); Franz Birke, Ingelheim (DE); Thierry Bouyssou, Mietingen (DE); Horst Dollinger, Schemmerhoffen (DE); Domnic Martyres, Biberach (DE); Pascale Pouzet, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 469 days.

(21) Appl. No.: 10/990,059

(22) Filed: Nov. 16, 2004

(65) Prior Publication Data

US 2005/0153979 A1      Jul. 14, 2005

Related U.S. Application Data

(60) Provisional application No. 60/528,619, filed on Dec. 11, 2003.

(30) Foreign Application Priority Data

Nov. 17, 2003   (EP) ................... 03026170

(51) Int. Cl.
     *C07D 401/00* (2006.01)
(52) U.S. Cl. ................... 546/201
(58) Field of Classification Search ............ 546/201
     See application file for complete search history.

(56) References Cited

U.S. PATENT DOCUMENTS

| | | | |
|---|---|---|---|
| 5,521,197 A | 5/1996 | Audia | |
| 5,962,473 A | 10/1999 | Johnson et al. | |
| 6,476,051 B2 | 11/2002 | Mattson et al. | |
| 6,683,096 B2 | 1/2004 | Santacana et al. | |
| 6,743,809 B2 | 6/2004 | Felding et al. | |
| 6,916,822 B2 * | 7/2005 | Tsushima et al. | 514/279 |
| 7,157,471 B2 * | 1/2007 | Anderskewitz et al. | 514/322 |
| 2004/0102450 A1 | 5/2004 | Ewing et al. | |
| 2006/0247230 A1 * | 11/2006 | Martyres et al. | 514/222.2 |

FOREIGN PATENT DOCUMENTS

| | | |
|---|---|---|
| WO | WO 98/02151 | 1/1998 |
| WO | WO 98/06402 | 2/1998 |
| WO | WO 98/11895 | 3/1998 |
| WO | WO 99/17773 | 4/1999 |
| WO | WO 99/37304 | 7/1999 |
| WO | WO 00/75130 A1 | 12/2000 |
| WO | WO 01/43740 A1 | 6/2001 |
| WO | WO 01/60796 A1 * | 8/2001 |
| WO | WO 02/08223 A1 | 1/2002 |

OTHER PUBLICATIONS

F. Z. Dorwald "Side Reactions in Organic Synthesis: A Guide to Successful Synthesis Design" 2005 Wiley-VCH Verlag GmbH & Co. KGaA, Weinheim.*

* cited by examiner

*Primary Examiner*—Rita J Desai
*Assistant Examiner*—John Mabry
(74) *Attorney, Agent, or Firm*—Michael P. Morris; Mary-Ellen M. Devlin; Philip I. Datlow

(57) ABSTRACT

Accordingly, one object of the present invention are novel piperidine-substituted indoles- or heteroderivatives thereof of the formula 1:

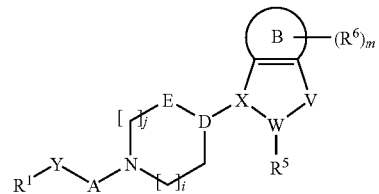

wherein $R^1$, $R^5$, $R^6$, A, B, D-E, X-W-V, Y, i, j, n and m are defined as below.

Another object of the present invention is to provide agonists or antagonists of CCR-3, or pharmaceutically acceptable salts thereof, more particularly to provide pharmaceutical compositions comprising a pharmaceutically acceptable carrier and a therapeutically effective amount of at least one of the compounds of the present invention or a pharmaceutically acceptable salt thereof.

15 Claims, No Drawings

PIPERIDINE-SUBSTITUTED INDOLES-OR HETERODERIVATIVES THEREOF

RELATED APPLICATIONS

This application claims benefit from U.S. Provisional Application No. 60/528,619, filed Dec. 11, 2003.

BACKGROUND OF THE INVENTION

1. Technical Field

This invention relates generally to piperidine-substituted indoles- or heteroderivatives thereof and their use as modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

2. Background Information

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-la, MIP-1 β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils.

There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR1 (or "CKR-1" or "CC-CKR-1") [MIP-la, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-la, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-Ia, RANTES, MIP-Ip] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpes viruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors.

Receptor expression may be permissive for infection by allowing for the subversion of normal immune system surveillance and response to infection. Additionally, human chemokine receptors, such as CXCR-4, CCR-2, CCR-3, CCR-5 and CCR-8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR-3 expressing cells by HIV or in preventing the manipulation of immune cellular responses by viruses such as cytomegaloviruses.

3. Background Art

U.S. Pat. No. 5,521,197 discloses piperidine-substituted indoles as 5-$HT_{1F}$ agonists.

The international patent application WO 98006402 discloses the use of these compounds for the treatment of cold or allergic rhinitis.

WO 98011895 discloses these compounds for the treatment of migraine.

Similar compounds are disclosed by WO 2001043740 also used as 5-HT modulators.

WO 2002008223 discloses piperidine-substituted indoles linked to peptide substituted aryl rings as $D_4$ modulators, but also with partially effect at the 5-$HT_{2A}$ or the 5-$HT_{2C}$ receptor.

WO 99037304 discloses substituted piperidine- and piperazine-derivatives for the inhibition of the Factor $X_A$.

WO 2000075130 discloses indoylpiperidine derivatives as antihistaminic and antiallergic agents, what comprises the treatment of bronchial asthma.

The problem underlying the present invention was the provision of novel CCR-3 modulators. It has been found surprisingly that certain piperidine-substituted indoles are highly suitable as CCR-3 modulators.

BRIEF SUMMARY OF THE INVENTION

Accordingly, one object of the present invention are novel piperidine-substituted indoles- or heteroderivatives thereof of the formula 1:

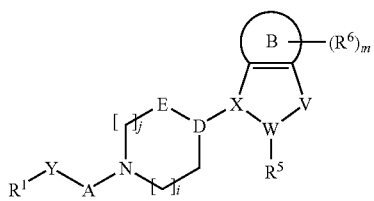

wherein $R^1$, $R^5$, $R^6$, A, B, D-E, X—W—V, Y, i, j and m are defined as below.

Another object of the present invention is to provide agonists or antagonists of CCR-3, or pharmaceutically acceptable salts thereof, more particularly to provide pharmaceutical compositions comprising a pharmaceutically acceptable carrier and a therapeutically effective amount of at least one of the compounds of the present invention or a pharmaceutically acceptable salt thereof. These and other objects, which will become apparent during the following detailed description.

DETAILED DESCRIPTION OF THE INVENTION

The present invention relates to compounds of formula 1,

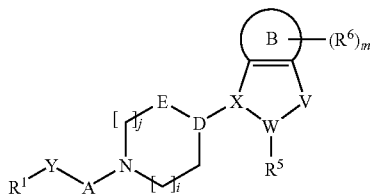

wherein $R^1$ is aryl, het or a annelated species thereof, wherein het is a heterocyclic ring and the annelated species comprises aryl-het-, het-aryl- or het-het-annelations, each of said aryl or het may be substituted with one, two or three $R^2$;

$R^2$ are each independently $C_{1-6}$-alkyl, $C_{3-6}$-cycloalkyl, $C_{1-6}$-haloalkyl, $C_{1-6}$-aralkyl, halogen, CN, $COOR^3$, $COR^3$, $CONR^3R^4$, $NR^3R^4$, $NR^3SO_2R^4$, $OR^3$, $NO_2$, $SR^3$, $SOR^3$, $SO_2R^3$ or $SO_2NR^3R^4$;

$R^3$ is H, $C_{1-6}$-alkyl, $C_{3-8}$-cycloalkyl or ($C_{3-8}$-cycloalkyl)-$C_{1-6}$-alkyl;

$R^4$ is H, $C_{1-6}$-alkyl, $C_{3-8}$-cycloalkyl or ($C_{3-8}$-cycloalkyl)-$C_{1-6}$-alkyl or $R^3$ and $R^4$ together with the interjacent nitrogen atom or $N$—$SO_2$— group form an optionally substituted nitrogen containing heterocyclic 3 to 8 membered ring $R^5$ is $C_{1-6}$-alkyl, $C_{1-6}$-alkoxy, $C_{1-6}$-acyloxy, $C_{1-6}$-aralkyl, $C_{3-6}$-cycloalkyl, ($C_{3-6}$-cycloalkyl)-$C_{1-6}$-alkyl, $C_{1-6}$-haloalkyl, $C_{1-6}$-thioalkyl, halogen, $NO_2$, CN;

$R^6$ are each independently $C_{1-6}$-alkyl, $C_{1-6}$-alkoxy, $C_{1-6}$-acyloxy, $C_{1-6}$-aralkyl, $C_{3-6}$-cycloalkyl, $C_{1-6}$-haloalkyl, $C_{1-4}$-thioalkyl, halogen, $OR^3$, $SR^3$, CN, $NO_2$, $COOR^3$, $COR^3$, $CONR^3R^4$, $NR^3R^4$, $NR^3COR^4$, $NR^3SO_2R^4$, $SOR^3$, $SO_2R^3$, $SO_2NR^3R^4$, aryl or het;

A is ($C_{3-6}$-cycloalkyl)-$C_{2-8}$-alkylene, straight or branched chain $C_{2-8}$-alkylen, optionally substituted with halogen or OH;

B is aryl or het;

D-E is CH—$CH_2$— or C=CH—

X—W—V is N—C=$CR^7$ or C=C—$NR^7$;

$R^7$ is H or $C_{1-6}$-alkyl;

Y is $CF_2$, $NR^4$, O, $S(O)_n$;

i, j are each independently 0, 1 or 2;

n is 0, 1 or 2;

m is 0, 1, 2, 3 or 4;

and pharmaceutically acceptable salts thereof.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

The term "aryl" as used herein, either alone or in combination with another substituent, means either an aromatic monocyclic system or aromatic multicyclic systems containing carbon atoms. For example, aryl includes a phenyl or a naphthyl ring system, wherein aryl means generally an aromatic system, for example phenyl.

The term "het" as used herein, either alone or in combination with another substituent, means a monovalent substituent derived by removal of a hydrogen from a five-, six- or seven-membered saturated or unsaturated (including aromatic) heterocycle containing carbon atoms and one, two, three or four ring heteroatoms selected from nitrogen, oxygen and sulfur. Examples of suitable heterocycles include: tetrahydrofuran, thiophene, diazepine, isoxazole, piperidine, dioxane, morpholine, piperazine or

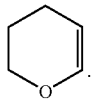

Although generally covered under the term "het", the term "heteroaryl" as used herein precisely defines an unsaturated heterocycle for which the double bonds form an aromatic system. Suitable example of heteroaromatic system include: pyridine, pyrimidine,

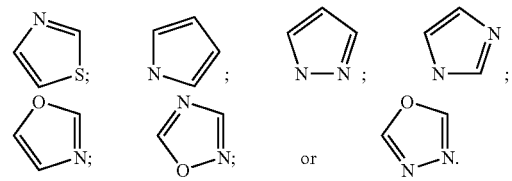

The term "annelated species of aryl or het" as used herein, either alone or in combination with another substituent wherein the annelated species presents as a aryl-het (a), a het-aryl (b) or a het-het (c) annelation means a monovalent substituent derived by removal of one hydrogen from a) an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or b) a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or c) a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "—$C_{1-6}$-alkyl" as used herein, either alone or in combination with another substituent, means acyclic, straight or branched chain alkyl substituents containing from one to six carbon atoms and includes, for example, methyl, ethyl, propyl, butyl, hexyl, 1-methylethyl, 1-methylpropyl, 2-methylpropyl or 1,1-dimethylethyl.

The term "—$C_{3-8}$-cycloalkyl" as used herein, either alone or in combination with another substituent, means a cycloalkyl substituent containing from three to six carbon atoms and includes cyclopropyl, cyclobutyl, cyclopentyl or cyclohexyl.

The term "—$C_{1-6}$-haloalkyl" as used herein, either alone or in combination with another substituent, means acyclic, straight or branched chain alkyl substituents containing up to six carbon atoms having one or more hydrogens substituted for a halogen selected from bromo, chloro, fluoro or iodo. Accordingly "—$C_{2-6}$-haloalky" has the same meaning with exception that the chain contains two to six carbon atoms. Preferably the term $C_{1-6}$-haloalkyl represents $C_{1-6}$-fluoroalkyl such as trifluoromethyl, 2,2,2-trifluoroethyl or perfluoroethyl.

The term "—$C_{1-6}$-alkoxy" as used herein, either alone or in combination with another substituent, means the substituent $C_{1-6}$-alkyl-O— wherein alkyl is as defined above containing up to six carbon atoms. Alkoxy includes methoxy, ethoxy, propoxy, 1-methylethoxy, butoxy or 1,1-dimethylethoxy. The latter substituent is known commonly as t-butoxy.

The term "—$C_{1-6}$-acyloxy" as used herein, either alone or in combination with another substituent, means the substituent $C_{1-6}$-alkyl-(CO)O— wherein alkyl is as defined above containing up to six carbon atoms. Acyloxy includes MeCOO—, EtCOO—, $^n$PrCOO—, $^i$PrCOO—, $^n$BuCOO—, $^{sec}$BuCOO— or $^{tert}$BuCOO—.

The term "—$C_{1-6}$-aralkyl" as used herein, either alone or in combination with another substituent, means the substituent -Aryl-$C_{1-6}$-alkyl- wherein alkyl is as defined above containing up to six carbon atoms. Aralkyl includes benzyl, phenylethyl, phenylpropyl, 1-phenyl-1-methylethyl, phenylbutyl or 1-phenyl-1,1-dimethylethoxy.

The term "—$C_{1-6}$-thioalkyl" as used herein, either alone or in combination with another substituent, means acyclic, straight or branched chain alkyl substituents containing up to six carbon atoms and a thiol (HS) group as a substituent. An example of a thioalkyl group is a thiopropyl, e.g., HS—$CH_2CH_2CH_2$—.

The term "—$C_{2-8}$-alkylene" as used herein means a divalent alkyl substituent derived by the removal of one hydrogen atom from each end of a saturated straight or branched chain aliphatic hydrocarbon containing from two to eight carbon atoms and includes, for example, $CH_2CH_2C(CH_3)_2$ $CH_2CH_2$—. Accordingly "—$C_{1-3}$-alkylene" has the same meaning with exception that the chain contains one to three carbon atoms.

PREFERRED EMBODIMENTS

Preferred are compounds of formula 1, wherein Y is S or S═O and R', $R^5$, $R^6$, A, B, D-E, X—W—V, i, j and m are defined as above. Particularly preferred are compounds of formula 1a or 1b,

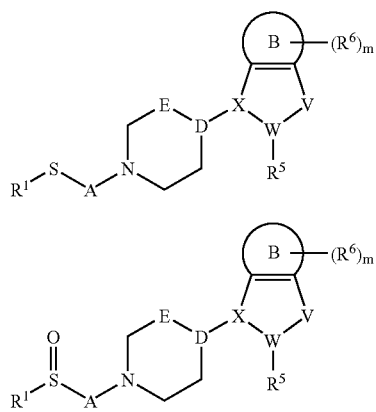

1a

1b wherein $R^1$, $R^5$, $R^6$, A, B, D-E, X—W—V and m are defined as above.

Also preferred are compounds of the formula 1, 1a or 1b wherein:
$R^1$ is aryl or het, both optionally substituted with one, two or three $R^2$ and
B is phenyl.

Also preferred are compounds of the formula 1, 1a or 1b wherein:
$R^1$ is phenyl, optionally substituted with one, two or three $R^2$ and
B is phenyl.

Also preferred are compounds of the formula 1, 1a or 1b wherein:
B is phenyl and
D-E is CH—$CH_2$—.

Also preferred are compounds of the formula 1, 1a or 1b wherein:
$R^1$ is phenyl, optionally substituted with one, two or three $R^2$ and
B is phenyl and
D-E is CH—$CH_2$—.

Also preferred are compounds of the formula 1, 1a or 1b wherein:
$R^1$ is phenyl, optionally substituted with one, two or three $R^2$ and
B is phenyl and
D-E is CH—$CH_2$— and
A is $CH_2$—$CH_2$—$CH_2$—.

Also preferred are compounds of the formula 1, 1a or 1b wherein:
$R^1$ is phenyl, optionally substituted with one, two or three $R^2$ and
B is phenyl and
D-E is CH—$CH_2$— and
A is $C(CH_3)_2$—$CH_2$—$CH_2$—.

Also preferred are compounds of the formula 1, 1a or 1b wherein:
$R^1$ is phenyl, optionally substituted with one, two or three $R^2$ and
B is phenyl and
D-E is CH—$CH_2$— and A is 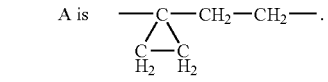.

Also preferred are compounds of the formula 1, 1a or 1b wherein:
$R^1$ is phenyl, optionally substituted with one, two or three $R^2$ and
B is phenyl and
D-E is CH—$CH_2$— and A is 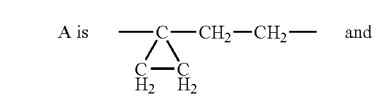 and $R^7$ is H Also preferred are compounds of the formula 1, 1a or 1b wherein:
$R^1$ is phenyl, optionally substituted with one, two or three $R^2$ and
B is phenyl and
D-E is CH—$CH_2$— and A is 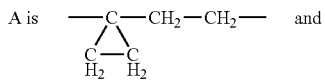 and R⁷ is Me Also preferred are compounds of the formula 1, 1a or 1b wherein:
R¹ is phenyl, optionally substituted with one, two or three R² and
B is phenyl and
D-E is C=CH—.

Also preferred are compounds of the formula 1, 1a or 1b wherein:
R¹ is phenyl, optionally substituted with one, two or three R² and
B is phenyl and
D-E is C=CH— and
A is CH₂—CH₂—CH₂—.

Also preferred are compounds of the formula 1, 1a or 1b wherein:
R¹ is phenyl, optionally substituted with one, two or three R² and
B is phenyl and
D-E is C=CH— and
A is C(CH₃)₂—CH₂—CH₂—.

Also preferred are compounds of the formula 1, 1a or 1b wherein:
R¹ is phenyl, optionally substituted with one, two or three R² and
B is phenyl and
D-E is C=CH— and A is 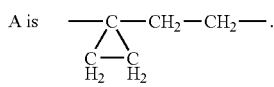.

Also preferred are compounds of the formula 1, 1a or 1b wherein:
R¹ is phenyl, optionally substituted with one, two or three R² and
B is phenyl and
D-E is C=CH— and A is 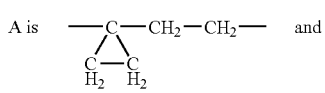 and R⁷ is H Also preferred are compounds of the formula 1, 1a or 1b wherein:
R¹ is phenyl, optionally substituted with one, two or three R² and
B is phenyl and
D-E is C=CH— and A is 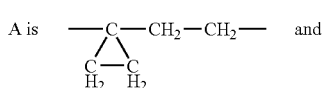 and R⁷ is Me Also preferred are compounds of the formula 1, 1a or 1b wherein
R¹ is phenyl, optionally substituted with one, two or three R² and
R² are each independently COOR³, COR³, CONR³R⁴, NR³SO₂R⁴, SOR³, SO₂R³ or SO₂NR³R⁴; in particular COOR³ or SO₂R³;
R³ is H or $C_{1-6}$-alkyl; in particular H or Methyl;
R⁴ is H or $C_{1-6}$-alkyl; in particular H or Methyl;

Also preferred are compounds of the formula 1, 1a or 1b wherein
R¹ is phenyl, optionally substituted with one R² and
R² is COOR³ or SO₂R³;
R³ is H or Methyl;
R⁴ is H or Methyl;

Also preferred are compounds of the formula 1, 1a or 1b wherein:
R⁵ is $C_{1-6}$-alkyl, $C_{3-6}$-cycloalkyl or $C_{2-6}$-haloalkyl; or
R² is CF₃ or halogen, in particular fluorine; or
R⁶ is preferably halogen, in particular fluorine; or Also preferred is the process for preparing compounds of formula 1 or 1a characterised in that a compound of formula 2

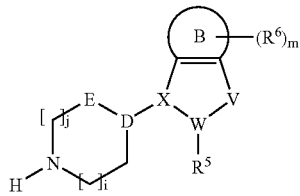

is reacted with a compound of the formula 3.

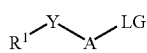

wherein R¹, R⁵, R⁶, A, B, X—W—V, i, j and m are defined as above and

LG is a suitable leaving group, in particular halogen, mesylate, triflate, tosylate or brosylate.

The compounds of formula 1 or 1a can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991).

The compounds of the instant application are useful for manufacturing a medicament for the prevention and/or treatment of diseases wherein the activity of a CCR-3-receptor is involved.

Preferred is the manufacturing of a medicament for the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

Most preferred is the manufacturing of a medicament for the prevention and/or treatment of e.g. inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs.

Preparation

Nitrogen substituted compounds of the formula 2a are prepared by a reductive condensation of a ring B, substituted at least by one amino-function and a hydrogen in ortho-position, with a keto function of a protected azacyclus;

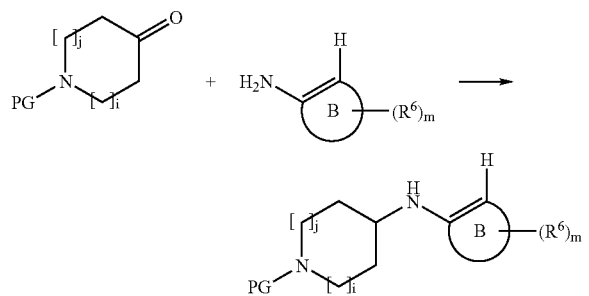

after coupling, the hydrogen atom is substituted via Friedel Crafts acylation by a α-halo-acetyl halide or a substituted α-halo-acetonitrile compound and thereafter hydrolysed to a α-keto compound;

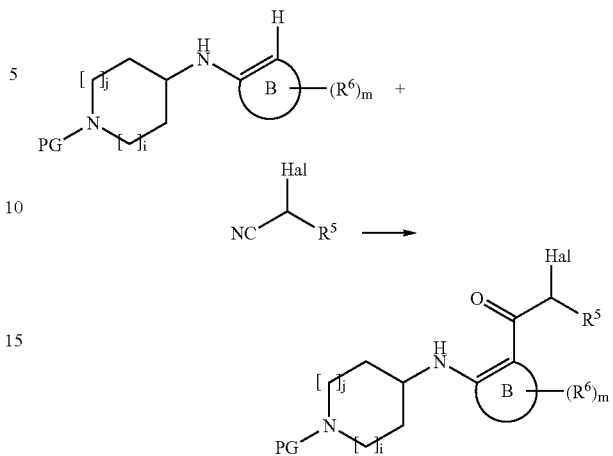

(Hal represents Cl or Br) after acylating reaction, ring closure in presence of an acid is promoted;

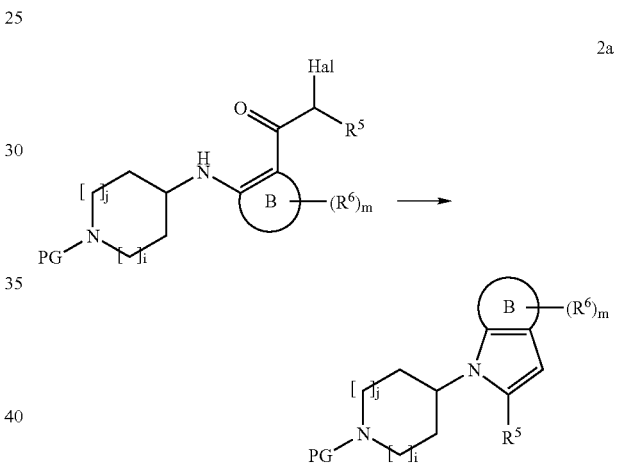

wherein the whole process $R^5$, $R^6$, B, i, j and m are defined as above and PG is a nitrogen protecting group, preferably a benzyl group Carbon substituted compounds of the formula 2c or 2d are prepared by a C—C coupling reaction under Buchwald conditions of a ring B, substituted at least by one nitro-function and a halogen in ortho-position, with a α-C-atom of a keto function,

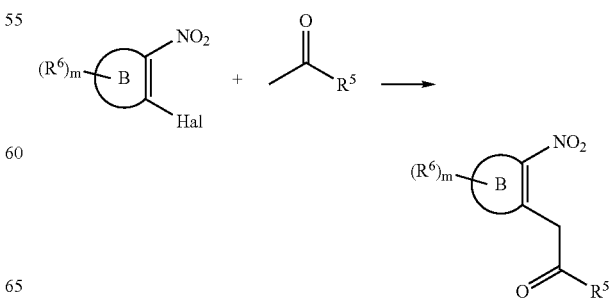

(Hal represents Cl or Br) after the coupling reaction a ring closure under reductive conditions is promoted,

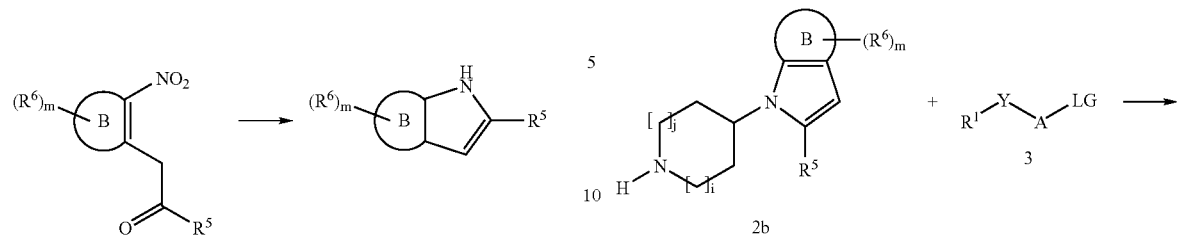

thereafter condensation of the newly formed ring, with the keto function of an azacyclus in the presence of a acid is promoted

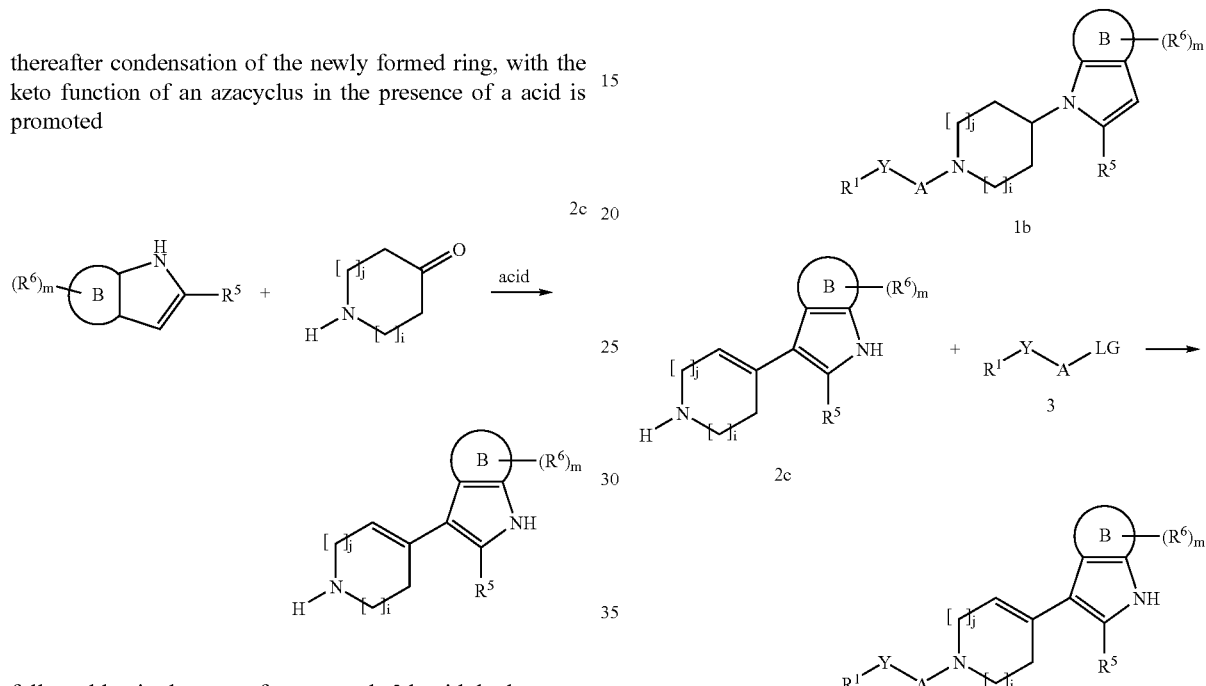

followed by, in the case of compounds 2d, with hydrogenation of the double bound of the azacyclus

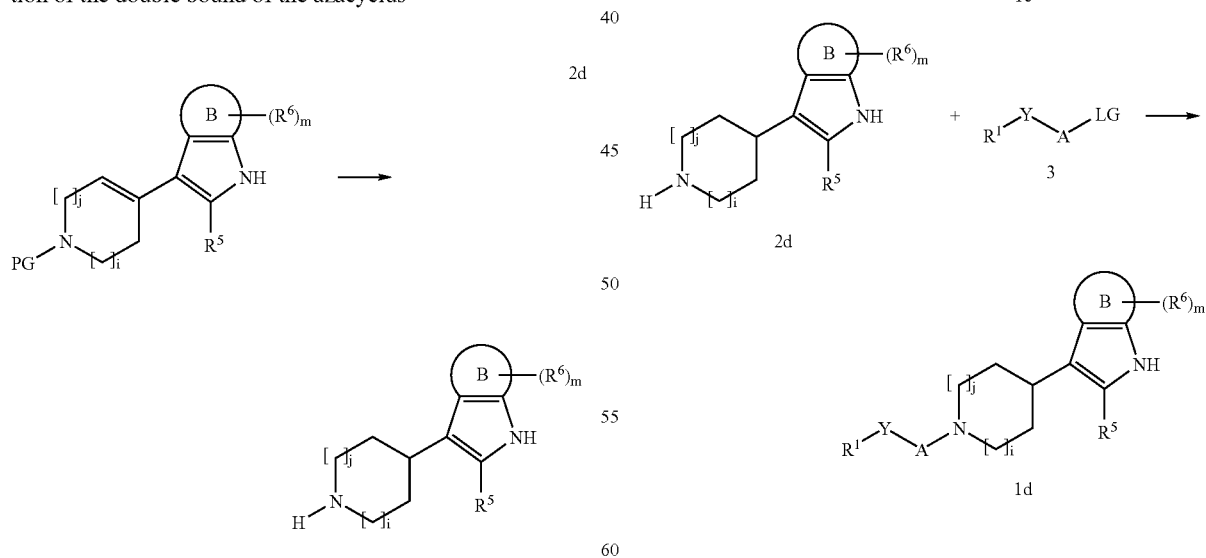

wherein the whole process $R^5$, $R^6$, B, D-E, i, j and m are defined as above.

Compounds of the formulae 1 b-d can be prepared by reacting compounds 2b-d with a compound of formula 3 wherein $R^1$, $R^5$, $R^6$, A, B, Y, i, j and m are defined as above; and

LG is a suitable leaving group, in particular halogen, mesylate, triflate, tosylate or brosylate.

N-Methylated species of the formulae 1e or 1f can be prepared by methylating compounds 1c or 1d.

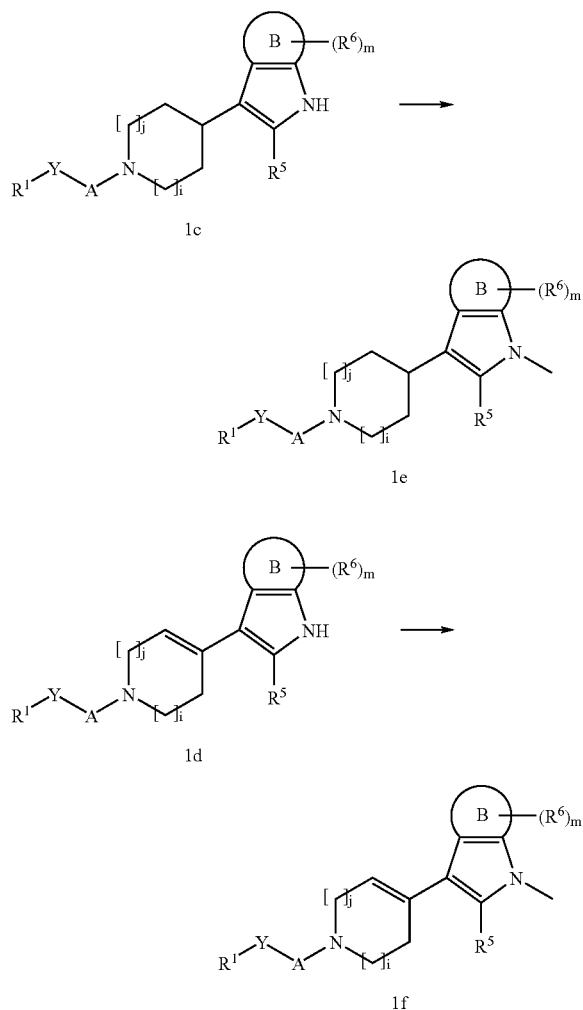

wherein $R^1$, $R^5$, $R^6$, A, B, Y, i, j and m are defined as above.

As will be appreciated by one of skill in the art, numerous modifications and variations of the present invention are possible in light of the above teachings. It is therefore to be understood that within the scope of the appended claims, the invention may be practiced otherwise than as specifically described herein.

EXAMPLE 1

1-(3-Bromo-propylsulfanyl)-4-fluoro-benzene

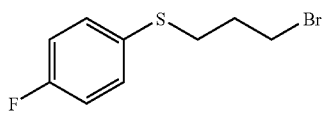

To a solution of p-fluoro-thiophenole (20.8 ml) and 1-3-dibromopropane (60 ml) in acetonitrile (250 ml) is added $K_2CO_3$ (55.0 g) in small quantities and the mixture refluxed for 3 hours. Thereafter the resulting salt and solvent are removed and the product distilled. Bp. 112-115° C./1 mbar.

EXAMPLE 2

(1-Benzyl-piperidine-4-yl)-(4-fluoro-phenyl)-amine

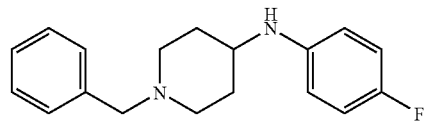

A solution of 4-fluoroaniline (32.7 g), N-benzylpiperidinone (106.0 g) and acetic acid (106.0 g) in 1,2-dichlorethane (1200 ml) is brought to a temperature below 15° C. To the stirred solution is added slowly a suspension of acetic acid (495.0 g) and sodium borohydride (31.2 g). After 2 h stirring at 15° C. and another 2 h at r.t., the solvent is removed in vacuo. Ethyl acetate (500 ml) and water (700 ml) are added under stirring and the resulting mixture is neutralised with sodium carbonate (ca. 250 g). The organic phase is separated, washed with a 2 M $NaHCO_3$ solution (100 ml) and water (100 ml) and dried with sodium sulphate. 53.8 g product is obtained as orange crystals after removal of the solvent and recrystallisation from ether/petroleum ether. Mp. 90-92° C.

EXAMPLE 3

1-[2-(1-Benzyl-piperidine-4-ylamino)-phenyl]-2-chloro-butan-1-one

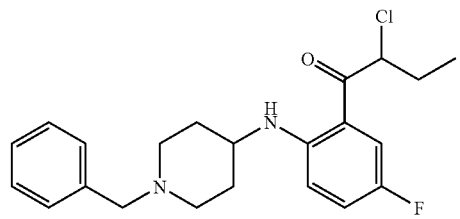

(1-Benzyl-piperidine-4-yl)-(4-fluoro-phenyl)-amine (51.2 g) is dissolved in 180 ml benzene and cooled down with an ice bath. Borontrichloride (180 ml, 1 M hexane solution) is added drop wise over 30 min. 2-Chlorbutyronitrile (18.6 g) and aluminiumtrichloride (24.0 g) are added and the resulting mixture is heated under reflux for 15 h. Then the mixture is cooled down, 180 ml of 2N HCl, are added and the mixture is further refluxed. 200 ml Water and 200 ml $CH_2Cl_2$ are added and the resulting mixture adjusted to pH=5 with portions of sodium carbonate. The phases are separated, the organic phase is dried with sodium sulphate and the solvent is removed. The resulting oil is purified with flash column chromatography (96:4 $CH_2Cl_2$:MeOH). Yield is 20.7 g of a colourless oil.

$^1$H NMR (300 MHz, $CDCl_3$): 1.10 (3H, t), 1.62-1.79 (3H, m), 2.01-2.36 (6H, m), 2.80-2.92 (2H, m), 3.43-3.57 (1H, m), 3.59 (2H, s), 5.03 (1H, dd), 6.75 (1H, dd), 7.16-7.22 (1H, m), 7.23-7.42 (4H, m), 7.43 (1H, dd), 8.92 (1H, br d).

EXAMPLE 4

1-(1-Benzyl-piperidine-4-yl)-2-ethyl-5-fluoro-1H-indole

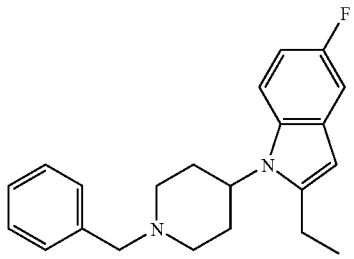

1-[2-(1-Benzyl-piperidine-4-ylamino)-phenyl]-2-chloro-butan-1-one (20.7 g) is mixed with 250 ml dioxane, 27 ml water and 2.3 g sodium borohydride and heated up to 120° C. After 12 h under reflux further 3.3 g of sodium borohydride are added and the mixture is refluxed for a further 16 h. After removal of the solvent, addition of 200 ml water and extraction with 150 ml CH$_2$Cl$_2$ of the mixture is performed, followed by drying with sodium sulphate and concentration in vacuo. The resulting oil is purified with flash column chromatography (96:4 CH$_2$Cl$_2$:MeOH). Yield is 11.9 g of a pale yellow oil.

$^1$H NMR (400 MHz, DMSO): 1.25 (3H, t), 1.72 (2H, br d), 2.19 (2H, br t), 2.39-2.48 (2H, m), 2.79 (2H, q), 2.98 (2H, br d), 3.59 (2H, s), 4.12-4.25 (1H, m), 6.19 (1H, s), 6.88 (1H, td), 7.19 (1H, dd), 7.21-7.31 (1H, m), 7.31-7.39 (4H, m), 7.49-7.52 (1H, m).

EXAMPLE 5

1-(Piperidine-4-yl)-2-ethyl-5-fluoro-1H-indole

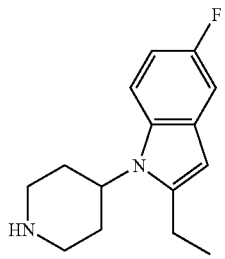

A solution of 1-(1-benzyl-piperidine-4-yl)-2-ethyl-5-fluoro-1H-indole (11.9 g) and acetic acid (4.1 ml) in methanol (250 ml) was hydrogenated for 8 h (50° C./1013 mbar). The mixture was then filtered and concentrated in vacuo. CH$_2$Cl$_2$ (250 ml), NaHCO$_3$ (100 ml) and water (300 ml) were added and the mixture stirred for 10 min. The organic layer was extracted with CHCl$_3$ and this was dried (MgSO4) and concentrated in vacuo. 6.4 g of pure product (73%) as colourless crystals was obtained by recrystallisation from ether/petroleum ether.

$^1$H NMR (400 MHZ, DMSO): 1.25 (3H, T), 1.65 (2H, BR D), 1.83 (1H, S), 2.22-2.37 (2H, M), 2.62 (2H, TD), 2.79 (2H, Q), 3.10 (2H, BR D), 4.20-4.31 (1H, M), 6.18 (1H, S), 6.83 (1H, TD), 7.19 (1H, DD), 7.59-7.14 (1H, M).

EXAMPLE 6

2-Ethyl-5-fluoro-1-{1-[3-(4-fluoro-phenylsulfanyl)-propyl]-piperidine-4-yl}-1H-indole

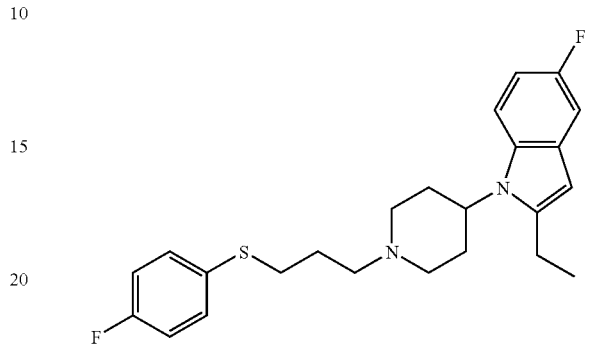

A mixture of 1-(1-Benzyl-piperidine-4-yl)-2-ethyl-5-fluoro-1H-indole (2.4 g), 1-(3-Bromo-propylsulfanyl)4-fluoro-benzene (2.4 g), acetonitrile and potassium carbonate is heated under reflux for 5 h. The solvent is removed and the resulting oil is purified with flash column chromatography (1:1 ethyl acetate:petrol ether). The fraction containing the product is freed from solvent and the resulting oil crystallized with ethanol. Yield is 1.2 g (30%) of colourless crystals.

M$_p$: 82-84° C.; $^1$H NMR (300 MHz, CDCl$_3$): 1.33 (3H, t, J 7.5), 1.77-1.87 (4H, m), 2.10 (2H, td, J 12.5, J 2.5), 2.48-2.66 (4H, m), 2.75 (2H, q, J 7.5), 2.94-3.08 (4H, m), 4.02-4.15 (1H, m), 6.20 (1H, s), 6.83 (1H, td, J 9.5, J 2.5), 6.98-7.04 (2H, m), 7.16 (1H, dd, J 9.5, J 2.5), 7.36-7.40 (2H, m), 7.47 (1H, dd, J 9.0, J 4.0). $^{13}$C NMR (75 MHz, CDCl$_3$): 13.23, 21.12, 26.95, 30.62, 33.10, 53.88, 54.11, 57.10, 98.85, 104.70, 105.00, 108.12, 108.46, 112.07, 115.98, 116.27, 129.30, 132.22, 132.33, 144.20, 156.05, 159.15, 160.21, 163.48.

EXAMPLE 7

1-(2-Nitro-4-fluoro-phenyl)-butan-2-one

To a solution of 1-bromo-2-nitro-4-fluoro-phenyl (6.2 g), Pd$_2$ dba$_3$ (260 mg), 2-dicyclohexylphosphino-2'-(N,N-dimethylamino)biphenyl (455 mg), K$_3$PO$_4$ (13.7 g) and 4-Methoxyphenol (700 mg) in toluene (60 ml) is added 2-butanone (5.6 ml) and the reaction mixture heated up to 60° C. for 24 hours under Argon. Thereafter the mixture is extracted with water and ethyl acetate (1:1), and washed with a 2M NaOH solution and water. The solvent is removed and the remaining product purified by flash chromatography (9:1 cyclohexene:ethyl acetate) to give 2.6 g (44%) of pure product as light yellow crystals.

¹H NMR (400 MHz, DMSO): 0.98 (3H, t), 2.56 (2H, q), 4.22 (2H, s), 7.51 (1H, dd), 7.63 (1H, td), 7.98 (1H, dd).

EXAMPLE 8

2-Ethyl-6-fluoro-1H-indole

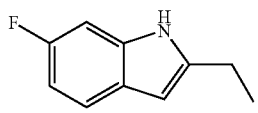

A solution of 1-(2-nitro-3-fluoro-phenyl)-butan-2-one (2.5 g) in ethanol (25 ml) is heated to 70° C. Na$_2$S$_2$O$_4$ (10.7 g) in water (30 ml) is added and the resulting mixture heated under reflux for 1 hour. The ethanol is removed by distillation, the residue extracted twice with ethyl acetate, the organic layer then washed with water and dried. The solvent is removed and the remaining product freed from impurities by flash chromatography (9:1 cyclohexane:ethyl acetate). 1.3 g (67%) of pure product is obtained as a white crystalline solid.

¹H NMR (400 MHz, DMSO): 1.26 (3H, t), 2.72 (2H, q), 6.12 (1H, s), 6.73-6.80 (1H, m), 7.02 (1H, br d), 7.37 (1H, dd), 10.98 (1H, br s).

EXAMPLE 9

2-Ethyl-6-fluoro-3-(1,2,3,6-tetrahydro-pyridin-4-yl)-1H-indole

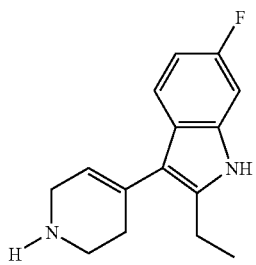

To a suspension of 2-ethyl-5-fluoro-1H-indole (1.2 g) in acetic acid (21 ml) at 90° C. is added a mixture of 4-piperidone (3.4 g) and 2N phosphoric acid (7 ml). The reaction mixture is stirred at 95° C. for 4 h, then water (50 ml) is added and the reaction allowed to cool to rt. The pH is adjusted to 11 with conc. NaOH solution and the mixture extracted into ethyl acetate. This is washed with water, dried over magnesium sulphate and concentrated in vacuo. The product is washed (ether) and dried over a suction filter, to give 1.5 g (84%) of product as a white crystalline solid. Mp. 194-6° C.

EXAMPLE 10

2-Ethyl-6-fluoro-3-[1-(4-flouro-phenyl-sulfanyl-propyl)-1,2,3,6-tetrahydro-pyridin-4-yl]-1H-indole

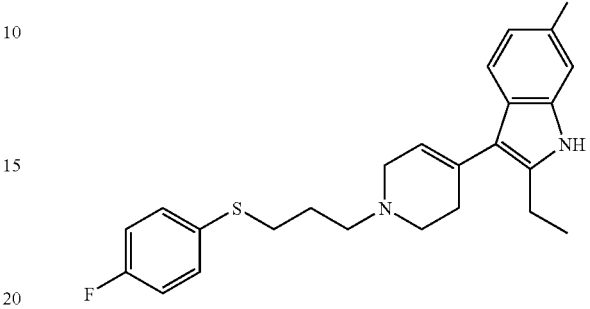

A solution of 2-ethyl-6-fluoro-3-(1,2,3,6-tetrahydro-pyridin-4-yl)-1H-indole (1.5 g), 1-(3-Bromo-propylsulfanyl)-4-fluoro-benzene (1.7 g), potassium iodide (20 mg) and potassium carbonate (1.1 g) in DMF (10 ml) is heated at 95° C. for 1 h. Ethyl acetate (80 ml) and water (35 ml) are then added and the organic phase is further extracted with ethyl acetate. The extracts are washed with water, dried (MgSO4) and concentrated in vacuo. The crude product is purified by flash chromatography (100:2 CH$_2$Cl$_2$:MeOH) and its hydrochloride salt is prepared by reaction in acetone with the appropriate amount of ethereal HCl, to give 1.7 g pure product (55%) as white crystals. Mp. 135° C.

EXAMPLE 11

2-Ethyl-6-fluoro-3-piperidin-4-yl-1H-indole

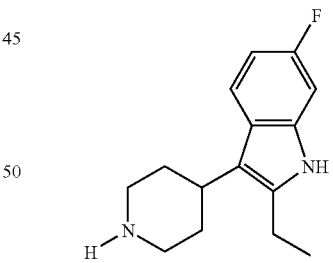

3-(1-Benzyl-1,2,3,6-tetrahydro-pyridin-4-yl)-2-ethyl-6-fluoro-1H-indole (1.4 g) is hydrogenated for 1 hour (r.t./1013 mbar) in the presence of 10% Pd/C catalyst (0.3 g) and methanol (25 ml). The catalyst is removed by filtration, the solvent evaporated and the residue washed with small portions of ether. 1.2 g (85%) of pure product is obtained.

¹H NMR (400 MHz, DMSO): 1.20 (3H, t), 1.52 (2H, br d), 1.90-2.04 (2H, m), 2.59-2.71 (4H, m), 2.71-2.83 (1H, m), 3.07 (2H, br d), 6.74 (1H, t), 6.99 (1H, d), 7.52-7.60 (1H, m), 10.72 (1H, br s).

EXAMPLE 12

2-Ethyl-6-fluoro-3-{1-[3-(4-fluoro-phenylsulfanyl)-propyl]-piperidin-4-yl}-1H-indole

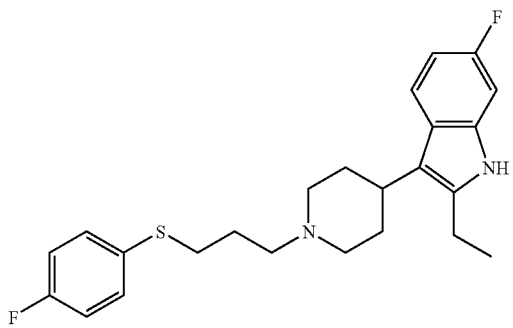

A mixture of 2-ethyl-6-fluoro-3-piperidin-4-yl-1H-indole (0.9 g), 1-(3-Bromo-propylsulfanyl)-4-fluoro-benzene (1.0 g), potassium iodide (20 mg) and potassium carbonate (0.7 g) in DMF (10 ml) is heated at 100° C. for 3 h, and allowed to cool to rt overnight. Ethyl acetate (50 ml) and water (25 ml) are added and the organic phase is washed with water, dried and concentrated in vacuo. The crude product is purified by flash chromatography (95:5 $CH_2Cl_2$:MeOH) and its hydrochloride salt is prepared by reaction in acetone with the appropriate amount of ethereal HCl giving, after recrystallisation from ether, 1.1 g pure product (70%) as white crystals.

$^1$H NMR (400 MHz, DMSO): 1.19 (3H, t), 1.75 (2H, br d), 1.92-2.02 (2H, m), 2.35 (2H, br q), 2.59 (2H, q), 2.92-3.09 (5H, m), 3.10-3.20 (2H, m), 3.47 (2H, br d), 6.71-6.79 (1H, m), 7.01 (1H, dd), 7.22 (2H, br t), 7.44-7.49 (2H, m), 7.58-7.62 (1H, m), 10.87 (1H, br s).

EXAMPLE 13

2-Ethyl-6-fluoro-3-{1-[3-(4-fluoro-phenylsulfanyl)-propyl]-piperidin-4-yl}-1-methyl-1H-indole

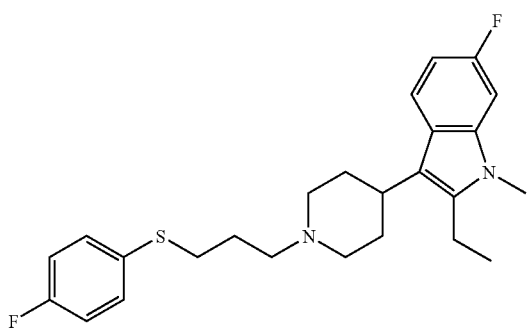

To a solution of 2-ethyl-6-fluoro-3-{1-[3-(4-fluoro-phenylsulfanyl)-propyl]-piperidin-4-yl}-1H-indole (0.4 g) in DMF (5 ml) at 5° C., is added sodium hydride (0.1 g) and the resulting mixture is stirred for 15 min at r.t. Thereafter the mixture is cooled to 5° C., MeI (0.1 ml) added and the mixture stirred for 30 min at r.t. Ethyl acetate (50 ml) and water (50 ml) are added and the organic layer is washed with water, dried over $MgSO_4$ and concentrated in vacuo. The hydrochloride salt is prepared by reaction in acetone with the appropriate amount of ethereal HCl giving, after recrystallisation from ether, 0.2 g pure product (46%) as white crystals.

$^1$H NMR (400 MHz, DMSO): 1.12 (3H, t), 1.74 (2H, br d), 1.92-2.01 (2H, m), 2.29-2.42 (2H, m), 2.78 (2H, q), 2.92-3.08 (5H, m), 3.10-3.17 (2H, m), 3.46 (2H, br d), 3.62 (3H, s), 6.79 (1H, br t), 7.18-7.27 (3H, m), 7.47 (2H, dd), 7.66 (1H, dd).

EXAMPLE 14-17

2-Ethyl-6-fluoro-3-{1-[3-(4-fluorophenylsulfanyl)-propyl]-1,2,3,6-tetrahydro-pyridin-4-yl}-1-methyl-1H-indole

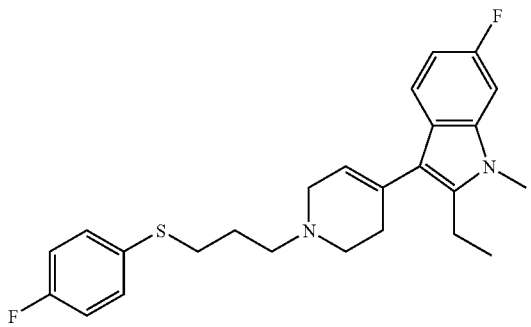

$^1$H NMR (400 MHz, DMSO): 1.19 (3H, t), 1.19-2.10 (2H, m), 2.50-2.62 (1H, m), 2.75-2.90 (3H, m), 3.05 (2H, t), 3.31-3.39 (3H, m), 3.56-3.63 (1H, m), 3.68 (3H, s), 3.70-3.81 (1H, m), 3.93-4.02 (1H, m), 5.62 (1H, br s), 6.86 (1H, br t), 7.22 (2H, t), 7.29 (1H, dd), 7.45-7.50 (3H, m).

2-Ethyl-5-fluoro-1-1-(3-p-trifluormethyl-phenyl-sulfanyl-propyl)-piperidin-4-yl]-1H-indole

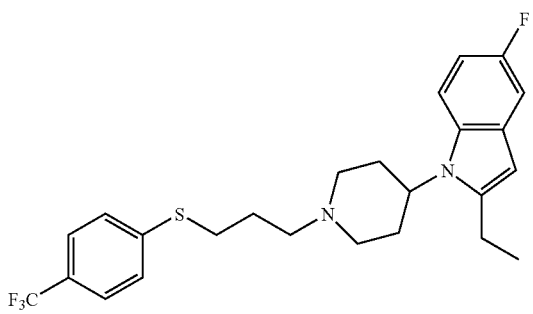

$^1$H NMR (400 MHz, DMSO): 1.25 (3H, t), 1.90 (2H, br d), 2.00-2.12 (2H, m), 2.66-2.83 (4H, m), 2.99-3.23 (6H, m), 3.51 (2H, br d), 4.47-4.60 (1H, m), 6.20 (1H, s), 6.83 (1H, td), 7.21 (1H, dd), 7.54 (2H, dd), 7.62-7.70 (3H, m).

23

2-Ethyl-5-fluoro-1 {1-[3-(4-fluoro-phenylsulfanyl)-3-methyl-butyl]-piperidin-4-yl}-1H-indole

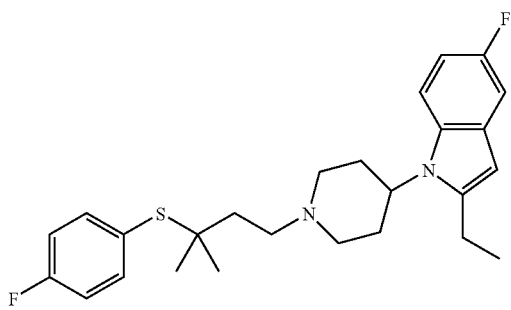

2-Ethyl-5-fluoro-1-(1-{2-[1-(4-fluoro-phenylsulfanyl)-cyclopropyl]-ethyl}piperidin-4-yl)-1H-indole

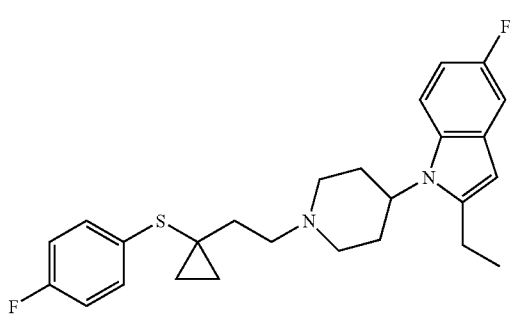

EXAMPLE 18-20

2-Ethyl-6-fluoro-3-[1-(3-p-trifluormethyl-phenyl-sulfanyl-propyl)-piperidin-4-yl]-1H-indole

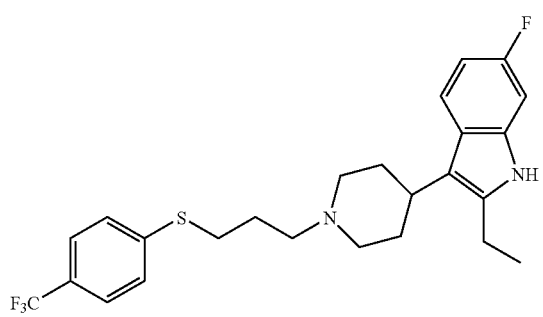

24

2-Ethyl-6-fluoro-3-{1-[3-(4-fluoro-phenylsulfanyl)-3-methyl-butyl]-piperidin-4-yl}-1H-indole

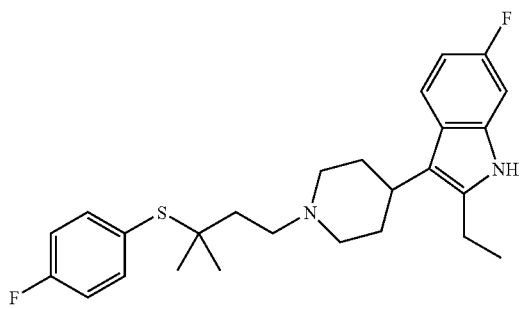

2-Ethyl-6-fluoro-3-(1-{2-[1-(4-fluoro-phenylsulfanyl)-cyclopropyl]-ethyl}piperidin-4-yl)-1H-indole

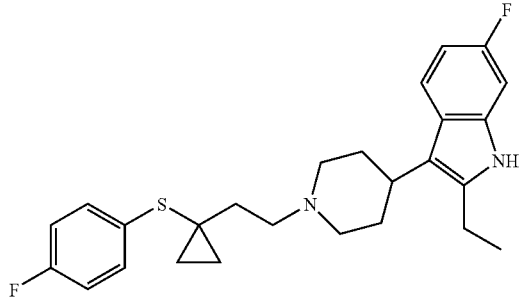

EXAMPLE 21-23

2-Ethyl-6-fluoro-1-methyl-3-[1-(3-p-trifluormethyl-phenyl-sulfanyl-propyl)-piperidin-4-yl]-1H-indole

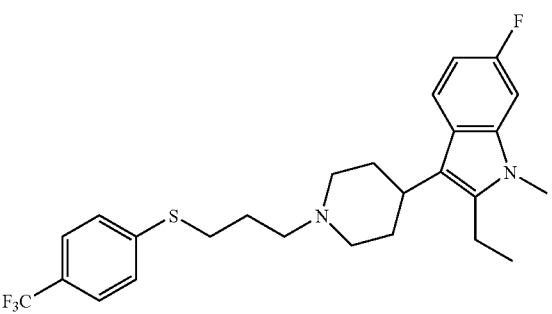

25

2-Ethyl-6-fluoro-3-{1-[3-(4-fluoro-phenylsulfanyl)-3-methyl-butyl]-piperidin-4-yl}1-methyl-1H-indole

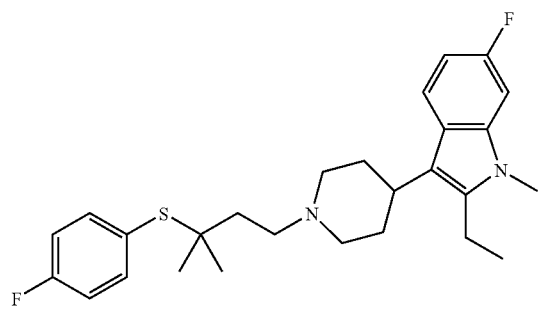

2-Ethyl-6-fluoro-3-(1-{2-[1-(4-fluoro-phenylsulfanyl)-cyclopropyl]-ethyl}-piperidin-4-yl)-1-methyl-1H-indole

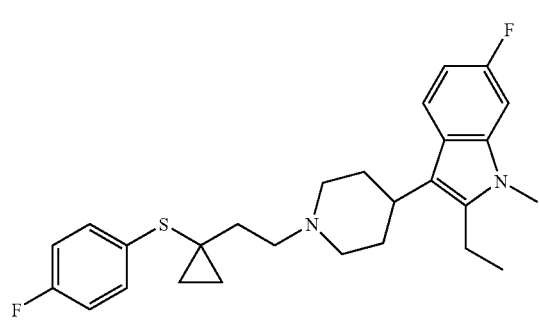

EXAMPLE 24-26

2-Ethyl-6-fluoro-3-[1-(3-p-trifluormethyl-phenyl-sulfanyl-propyl)-1,2,3,6-tetrahydro-pyridin-4-yl]-1H-indole

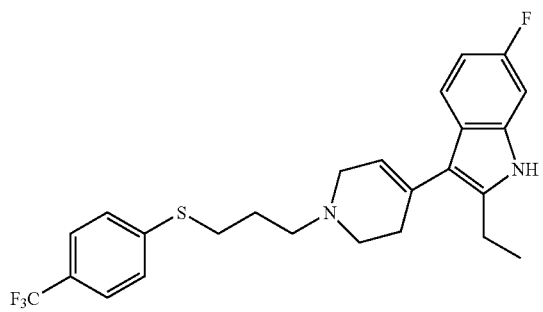

26

2-Ethyl-6-fluoro-3-{1-[3-(4-fluoro-phenylsulfanyl)-3-methyl-butyl]-1,2,3,6-tetrahydro-pyridin-4-yl}1H-indole

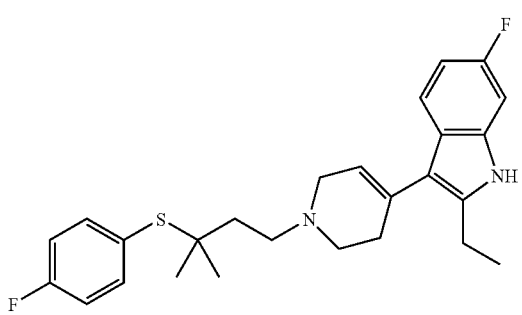

2-Ethyl-6-fluoro-3-(1-{2-[1-(4-fluoro-phenylsulfa-nyl)-cyclopropyl]-ethyl}-1,2,3,6-tetrahydro-pyridin-4-yl)-1H-indole

EXAMPLE 27-29

2-Ethyl-6-fluoro-1-methyl-3-[1-(3-p-trifluormethyl-phenyl-sulfanyl-propyl)-1,2,3,6-tetrahydro-pyridin-4-yl]-1H-indole

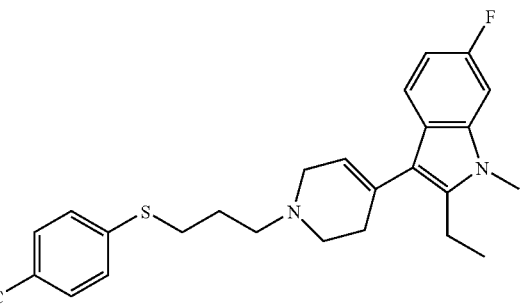

2-Ethyl-6-fluoro-3-{1-[3-(4-fluoro-phenylsulfanyl)-3-methyl-butyl]-1,2,3,6-tetrahydro-pyridin-4-yl}-1-methyl-1H-indole $^1$H NMR (400 MHz, DMSO): 1.22 (3H, t), 1.63 (2H, br d), 1.73-1.83 (2H, m), 1.98-2.11 (2H, m), 2.19-2.34 (2H, m), 2.43 (2H, t), 2.73 (2H, q), 2.83 (2H, br d), 3.15 (1H, t), 3.25-3.31 (1H, m), 4.08-4.19 (1H, m), 6.18 (1H, s), 6.86 (1H, td), 7.12 (1H, t), 7.17 (1H, dd), 7.37 (1H, dd), 7.42 (1H, dd), 7.82 (1H, d), 8.48 (1H, d).

2-{3-[4-(2-Ethyl-5-fluoro-indol-1-yl)-3,6-dihydro-2H-pyridin-1-yl]-propylsulfanyl}-thiazolo[5,4-b]pyridine

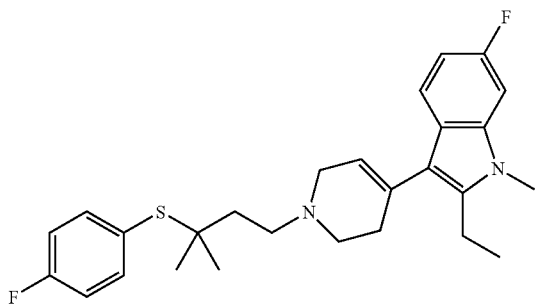

2-Ethyl-6-fluoro-3-(1-{2-[1-(4-fluoro-phenylsulfanyl)-cyclopropyl]-ethyl}-1,2,3,6-tetrahydro-pyridin-4-yl)-1-methyl-1H-indole

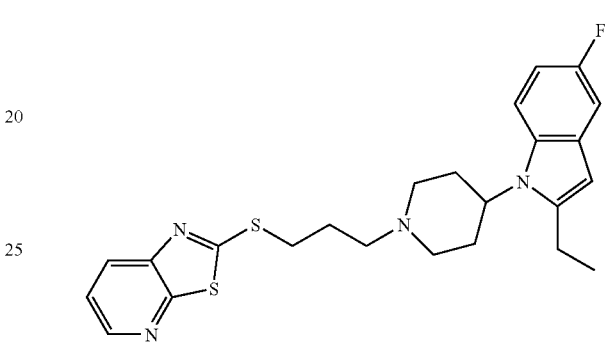

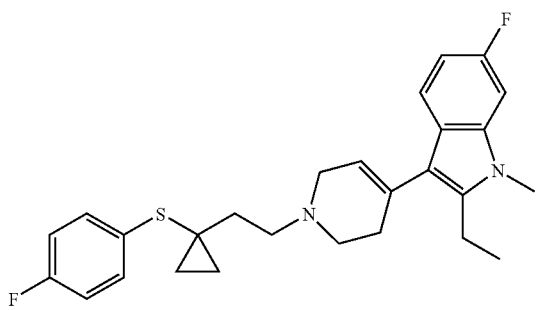

$^1$H NMR (400 MHz, DMSO): 1.25 (3H, t), 1.75 (2H, br d), 1.97-2.08 (2H, m), 2.20-2.33 (2H, m), 2.41-2.51 (2H, m), 2.56-2.65 (2H, m), 2.78 (2H, q), 3.12 (2H, br d), 3.49 (2H, t), 4.18-4.30 (1H, m), 6.20 (1H, s), 6.87 (1H, td), 7.19 (1H, dd), 7.48-7.53 (2H, m), 8.21 (1H, dd), 8.50 (1H, dd).

5-Chloro-2-{3-[4-(2-ethyl-5-fluoro-indol-1-yl)-piperidin-1-yl]-propylsulfanyl}-benzothiazole

EXAMPLE 30-37

3-{3-[4-(2-Ethyl-5-fluoro-indol-1-yl)-3,6-dihydro-2H-pyridin-1-yl]-propylsulfanyl}-[1,2,4]triazolo[4,3-a]pyridine

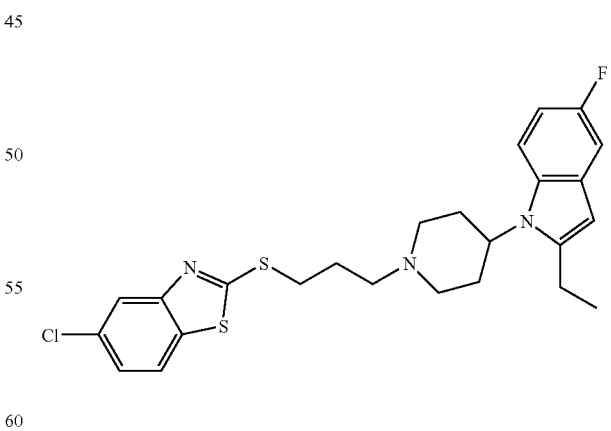

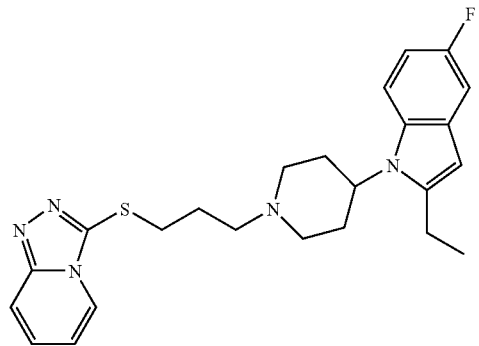

$^1$H NMR (400 MHz, DMSO): 1.25 (3H, t), 1.93 (2H, br d), 2.30-2.42 (2H, m), 2.81 (2H, q), 2.99 (2H, br q), 3.13-3.32 (4H, m), 3.56 (2H, t), 3.60-3.81 (2H, m), 4.53-4.65 (1H, m), 6.22 (1H, m), 6.82 (1H, br t), 7.21 (1H, dd), 7.43 (1H, dd), 7.91-8.02 (2H, m), 8.08 (1H, dd).

2-{3-[4-(2-Ethyl-5-fluoro-indol-1-yl)-3,6-dihydro-2H-pyridin-1-yl]-propylsulfanyl}benzooxazole

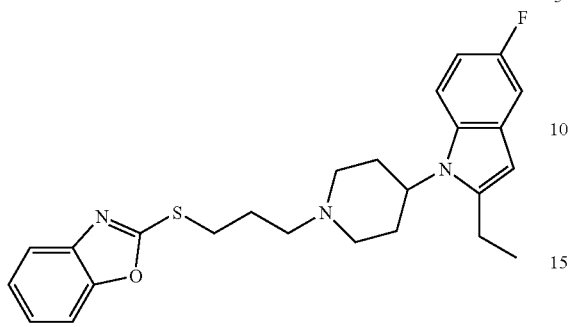

¹H NMR (400 MHz, DMSO): 1.27 (3H, t), 1.76 (2H, br d), 1.99-2.09 (2H, m), 2.19-2.27 (2H, m), 2.40-2.53 (2H, m), 2.59 (2H, t), 2.77 (2H, q), 3.11 (2H, br d), 3.43 (2H, t), 4.17-4.28 (1H, m), 6.20 (1H, s), 6.85 (1H, td), 7.18-7.22 (2H, m), 7.30-7.35 (2H, m), 7.47-7.55 (1H, m), 7.62-7.67 (1H, m).

2-Ethyl-5-fluoro-1-{1-[3-(5-trifluormethyl-pyridin-2-ylsulfanyl)-propyl]-1,2,3,6-tetrahydro-pyridin-4-yl}-1H-indole

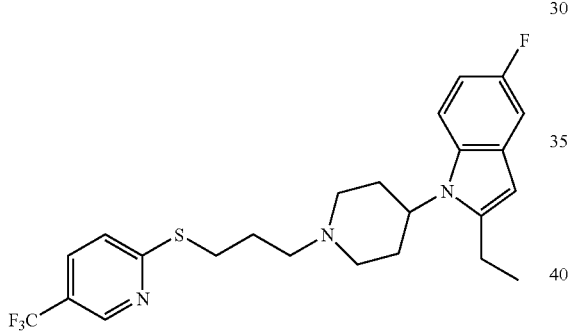

¹H NMR (400 MHz, DMSO): 1.25 (3H, t), 1.73 (2H, br d), 1.73-1.82 (2H, m), 2.12 (2H, br t), 2.32-2.44 (3H, m), 2.78 (2H, q), 3.02 (2H, br d), 3.24-3.32 (3H, m), 4.13-4.23 (1H, m), 6.20 (1H, s), 6.85 (1H, td), 7.20 (1H, dd), 7.46-7.51 (1H, m), 7.53 (1H, m), 7.99 (1H, dd), 8.81 (1H, s).

2-Ethyl-6-fluoro-3-{1-[3-(4-fluorophenylsufanyl)-propyl]piperidin-3-yl}-1H-indole

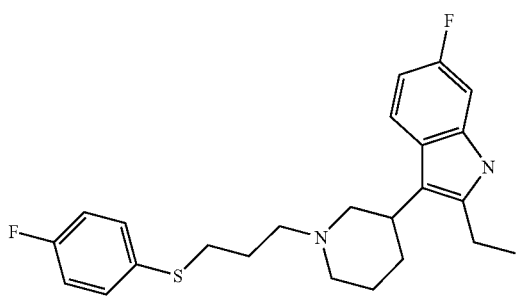

¹H NMR (400 MHz, DMSO): 1.19 (3H, t), 1.51-1.85 (6H, m), 1.96 (1H, br. t), 2.30-2.44 (3H, m), 2.64-2.72 (3H, m), 2.83-2.90 (2H, m), 2.93 (2H, t), 6.70-6.78 (1H, m), 6.99 (1H, dd), 7.13 (2H, t), 7.35-7.41 (2H, m), 7.49-7.54 (1H, m), 10.77 (1H, s).

3-{3-[4-(2-Ethyl-5-fluoro-indol-1-yl)-piperidin-1-yl]propylsulfanyl}-benzoic acid ethyl ester

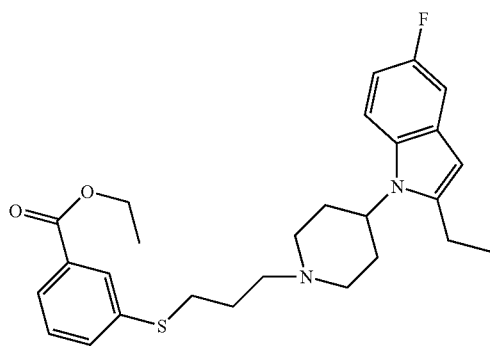

Mp. 179-181° C.

3-{3-[4-(2-Ethyl-5-fluoro-indol-1-yl)-piperidin-1-yl]propylsulfanyl}-benzoic acid

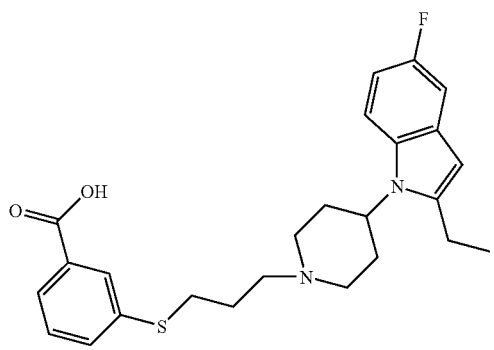

¹H NMR (400 MHz, DMSO): 1.25 (3H, t), 1.90 (2H, br. d), 1.98-2.10 (2H, m), 2.72-2.88 (4H, m), 3.02-3.21 (7H, m), 3.44-3.60 (2H, m), 4.53 (1H, br. s), 6.21 (1H, s), 6.88 (1H, td), 7.22 (1H, dd), 7.49 (1H, t), 7.68 (1H, br. d), 7.70-7.80 (2H, m), 7.88 (1H, s).

Method of Treatment

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversushost disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Pharmaceutical Forms

The compounds of formula 1 are administered to a mammal in a therapeutically effective amount. By "therapeutically effective amount" it is meant an amount of a compound of formula 1 that, when administered alone or in combination with an additional therapeutic agent to a mammal, is effective to prevent or ameliorate diseases, wherein the activity of a CCR-3-receptor is involved, or the progression of this disease.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermale routes, using transdermale skin patches. When administered in the form of a transdermale delivery system, the dosage administration will, of course, be continuous rather than intermittent throughout the dosage regimen.

The compounds of formula 1 are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and colouring agents can also be incorporated into the mixture. Suitable binders include starch, gelatine, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues.

Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and cross linked or amphipathic block copolymers of hydrogels.

Dosage forms (pharmaceutical compositions) suitable for administration may contain from about 1 milligram to about 100 milligrams of active ingredient per dosage unit.

In these pharmaceutical compositions the active ingredient will ordinarily be present in an amount of about 0.5-95% by weight based on the total weight of the composition.

Gelatine capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain colouring and flavouring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Where two or more of the foregoing second therapeutic agents are administered with the compound of formula 1, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of formula 1 and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

We claim:

1. A compound of formula 1

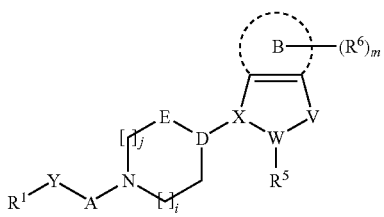

wherein
$R^1$ is phenyl, benzoxazole, benzothiazole, or thiazolo[5,4-b]pyridine, each of which may be substituted with one, two or three $R^2$;
$R^2$ are each independently $C_{1-6}$-alkyl, $C_{1-6}$-haloalkyl, halogen, or $COOR^3$;
$R^3$ is H, or $C_{1-6}$-alkyl;
$R^5$ is $C_{2-6}$-alkyl, $C_{1-6}$-alkoxy, $C_{1-6}$-acyloxy, $C_{1-6}$-aralkyl, $C_{3-6}$-cycloalkyl, ($C_{3-6}$-cycloalkyl)-$C_{1-6}$-alkyl, $C_{1-6}$-haloalkyl, $C_{1-6}$-thioalkyl, halogen, $NO_2$ or CN;
$R^6$ are each independently $C_{1-6}$-alkyl, $C_{1-6}$-haloalkyl, or halogen;
A is ($C_{3-6}$ cycloalkyl)-$C_{2-8}$-alkylene or straight or branched chain $C_{2-8}$-alkylene, each optionally substituted with halogen or OH;
B is phenyl;
D-E is CH—$CH_2$— or C=CH—;
X—W—V is N—C=$CR^7$ or C=C—$NR^7$;
$R^7$ is H or $C_{1-6}$-alkyl;
Y is $CF_2$, $NR^4$, O, $S(O)_n$;

i, j are each 1;
n is 0, 1 or 2;
m is 0, 1, 2, 3 or 4;
or a pharmaceutically acceptable salt thereof.

2. A compound of claim 1 of the formula 1a,

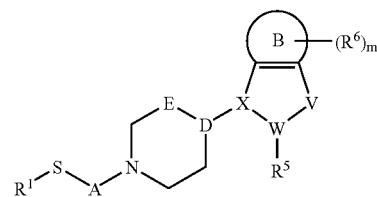

wherein $R^1$, $R^5$, $R^6$, A, B, D-E, X—W—V, and m are defined as in claim 1.

3. A compound of claim 1 of the formula 1b,

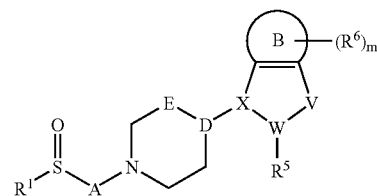

wherein $R^1$, $R^5$, $R^6$, A, B, D-E, X—W—V, and m are defined as in claim 1.

4. A compound according to claim 1, wherein
$R^1$ is phenyl, optionally substituted with one, two or three $R^2$.

5. A compound according to claim 1, wherein
D-E is CH—$CH_2$—.

6. A compound according to claim 1, wherein
A is $CH_2$—$CH_2$—$CH_2$—.

7. A compound according to claim 1, wherein
A is $C(CH_3)_2$—$CH_2$—$CH_2$—.

8. A compound according to claim 1, wherein

A is 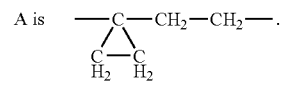

9. A compound according to claim 1, wherein
$R^5$ is $C_{2-6}$-alkyl, $C_{3-6}$-cycloalkyl or $C_{2-6}$-haloalkyl.

10. A compound according to claim 1, wherein
X—W—V is N—C=$CR^7$.

11. A compound according to claim 1, wherein $R^1$ is phenyl, optionally substituted with one, two or three $R^2$;
$R^2$ are each independently $COOR^3$; and
$R^3$ is H or $C_{1-6}$-alkyl.

12. A process for preparing a compound of formula 1 according to claim 1, said process comprising reacting a compound of formula 2

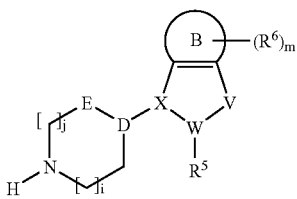

with a compound of the formula 3

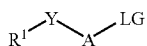

wherein $R^1$, $R^5$, $R^6$, Y, A, B, D-E, X—W—V, i, j and m are defined as in claim 1 and LG is a suitable leaving group selected from halogen, mesylate, triflate, tosylate or brosylate.

13. A composition comprising one or more compounds of formula 1 according to claim 1, and one or more pharmaceutically acceptable carriers.

14. A compound according to claim 1, wherein:
X—W—V is C=C—$NR^7$;
Y is $S(O)_n$; and
wherein $R^2$, $R^3$, $R^4$, $R^5$, $R^6$, A, D-E, $R^7$, n and m are defined as in claim 1;
or a pharmaceutically acceptable salt thereof.

15. A compound according to claim 1, wherein:
$R^1$ is phenyl, optionally substituted with one, two or three $R^2$;
$R^5$ is $C_{2-6}$-alkyl;
B is phenyl;
X—W—V is C=C—$NR^7$;
Y is $S(O)_n$; and
$R^2$, $R^3$, $R^6$, A, D-E, $R^7$, n and m are as defined in claim 1;
or a pharmaceutically acceptable salt thereof.

* * * * *